(12) United States Patent
Nimmannit et al.

(10) Patent No.: US 7,273,627 B2
(45) Date of Patent: Sep. 25, 2007

(54) BOTANICAL COMPOSITIONS HAVING HYPOGLYCEMIC, HYPOLIPIDEMIC AND ANTIMICROBIAL ACTIVITIES FOR MAINTAINING GOOD HEALTH IN NORMAL PERSON AND DIABETIC PATIENT

(76) Inventors: Sukanya Nimmannit, 386/ 2 Soi Ratchadaphisek 42, Chatuchak, Bangkok 10900 (TH); Apijade Jesadanont, 386/ 2 Soi Ratchadaphisek 42, Chatuchak, Bangkok 10900 (TH); Kamol Vichitpan, 41/267 M. 10 Teerakorn Vijitphan, Puttanmonthon 2 Road, Bang Pai, Bangkae, Bangkok 10160 (TH); Somlak Poungshompoo, 393 / 608 Badin Sweethome 2, Bld. D, Soi Ladpharo 112, Wangthonglang Dist., Bangkok 10310 (TH); Sunanta Pongsamart, 22 Soi Wat Apaitayaram, Rajvitee Road, Rajtevee, Bangkok 10400 (TH); Ampai Panthong, 126/50 Wangtal Villa, Moo 2, Padad, Muang, Chiangmai 50100 (TH); Pintip Pongpech, 100/1 Soi Patipat 6, Patipat Road, Rajtevee, Bangkok 10400 (TH); Boonyong Tantisira, 246 Soi Yasoop 1, Lardyao, Chatuchak, Bangkok 10900 (TH); Penphun Naenna, 213/1 Soi Paholyothin 1, Paholyothin Road, Rajtevee, Bangkok 10400 (TH); Chaiyasit Sittiwet, 169 Moo 7 Phosai, Srisomdej, Roi Et 45280 (TH); Aungkana Paopadetkarn, 97/131 Chompol Rd., Muang, Chachoengsao 24000 (TH)

( * ) Notice: Subject to any disclaimer, the term of this patent is extended or adjusted under 35 U.S.C. 154(b) by 0 days.

(21) Appl. No.: 10/894,075

(22) Filed: Jul. 20, 2004

(65) Prior Publication Data
US 2006/0018978 A1  Jan. 26, 2006

(51) Int. Cl.
*A61K 36/00* (2006.01)
(52) U.S. Cl. .................... 424/725; 424/774; 424/779
(58) Field of Classification Search .................... None
See application file for complete search history.

(56) References Cited

U.S. PATENT DOCUMENTS

| | | | | |
|---|---|---|---|---|
| 4,200,629 A | * | 4/1980 | Nakamura | 514/284 |
| 4,551,177 A | * | 11/1985 | Trubiano et al. | 106/206.1 |
| 5,856,487 A | * | 1/1999 | Upadhyay et al. | 546/48 |
| 6,136,833 A | * | 10/2000 | Badawy et al. | 514/378 |
| 6,218,183 B1 | * | 4/2001 | Kumar et al. | 435/420 |
| 6,485,759 B2 | | 11/2002 | Chantara et al. | |
| 2004/0191263 A1 | * | 9/2004 | Hageman et al. | 424/184.1 |

OTHER PUBLICATIONS

Singh et al. Int. J. Pharmacogn. 1994. vol. 32, No. 4, pp. 314-319.*

* cited by examiner

*Primary Examiner*—Christopher R. Tate

(57) ABSTRACT

Botanical compositions are described having hypoglycemic, hypolipidemic and antimicrobial activity for maintaining good health in normal person and diabetic person comprising water extract of two medicinal plants, dried leaves of *Malvastrum coromandelianum* and/or dried stems of *Coscinium fenestratum*. The extracts are used separately or in combination of fixed amount or varied amounts, as herbal beverage or in different pharmaceutical preparations.

4 Claims, 1 Drawing Sheet

BOTANICAL COMPOSITIONS HAVING HYPOGLYCEMIC, HYPOLIPIDEMIC AND ANTIMICROBIAL ACTIVITIES FOR MAINTAINING GOOD HEALTH IN NORMAL PERSON AND DIABETIC PATIENT

FIELD OF INVENTION

This invention relates to botanical composition for maintaining a healthy condition in normal people and treatment against infections including providing blood sugar and lipid lowering activity in diabetic patients and the process for preparing the same.

BACKGROUND OF THE INVENTION

At present, people all around the world turn more and more back to nature as it is now realized that there are still a lot of very good things the mother nature has given to mankind yet has never been explored or brought to use like medicinal herbal treatment to treat cases of hard-to-cure diseases such as cancer-the disease of various origins, immune-related diseases and even AIDS. The patients of these hard-to-cure diseases very often died very soon because of the radical treatment and the side effects of the westernized medication while the oriental way of treatment offers a more gentle, mild yet effective choice of medicinal herbs which possesses the so-called 'Yin-Yang' curing action. That is to say, while an agent in the medical recipe helps to suppress the evil or deteriorating causes in the body, the other agent(s) in the same recipe would also promote the well-being of the good cells or healthy elements of such a person, U.S. Pat. No. 6,485,759B2. This is obviously shown in many circumstances and the contrary is clear when a patient has been treated using only the western scientific way of treatment where a synthetic agent used mostly suppresses the causative agent of the disease as well as the host good cells, since the western way of treatment is quite "non-selective". Thus presently, even the renowned medical schools turn to pay greater attention to the oriental way of treatment with the hope to reach the best and optimized way combined for treatment of the symptom of a patient.

The invention described here is a pharmaceutical product of medicinal herbal origin for maintaining good health in a healthy person as well as in diabetic patient. As it is well-known that sugar especially glucose although regarded as a major source of energy and as structural elements in the body, too much of sugar intake leads to numerous diseases such as hyperlipidemia especially hypertriglyceridemia as the carbon component of glucose is very efficiently converted to fatty acids and thus to triglyceride leading to severe heart diseases and strokes which are even more dangerous than hypercholesterolemia in a normal individual. More serious is in diabetic patients whose high level of glucose in blood resulting in too many deteriorating complications occurred probably through glycosylation of membrane such as diabetic retinopathy, nephropathy and more. Keeping blood glucose at normal level has been shown to prevent efficiently such complication at a great extent. Most important of all is that even very small wound can always lead to death due to serious infections or resulting in lower extremities amputation (LEA) surgery and thus disability of the diabetic patients. It would be thus most desirable to have a medicinal composition possesses both anti-infectious and hypoglycemic activity including hypolipidemic activity. The invention described presently offers a most cost-effective formulation for maintaining good health in diabetic patients as well as in normal people and perhaps those with immune-compromised to a certain extent since the preparation has very good activity against the pus-forming microbe-*Staphylococcus aureus* of both methicillin-sensitive and methicillin-resistant strains, and a few pathogenic microorganisms including *Salmonella typhimurium*. Moreover, the plant extract composition possesses very good hypoglycemic and hypolipidemic activity. Drinking water extract of *Malvastrum coromandelianum* caused within 7 days very good healing of severe ulcerative wound in a diabetic patient who was about to undergo leg amputation surgery and the patient could avoid leg surgery thereafter.

SUMMARY

Botanical compositions are described having hypoglycemic, hypolipidemic and antimicrobial activity for maintaining good health in normal person and diabetic person comprising water extract of medicinal plants, dried leaves of *Malvastrum coromandelianum* (Linn.) Garcke, with or without the combination with dried stems of *Coscinium fenestratum* (Gaerth.) Colebr. The pharmaceutical preparations are decoction, solution, granules, tablet, capsule, reconstitute preparation or any appropriate dosage forms. The two extracts may be used separately or in combination of fixed amount or varied amounts, as herbal beverage or in different pharmaceutical preparations.

DETAILED DESCRIPTION OF THE INVENTION

Figure 1:
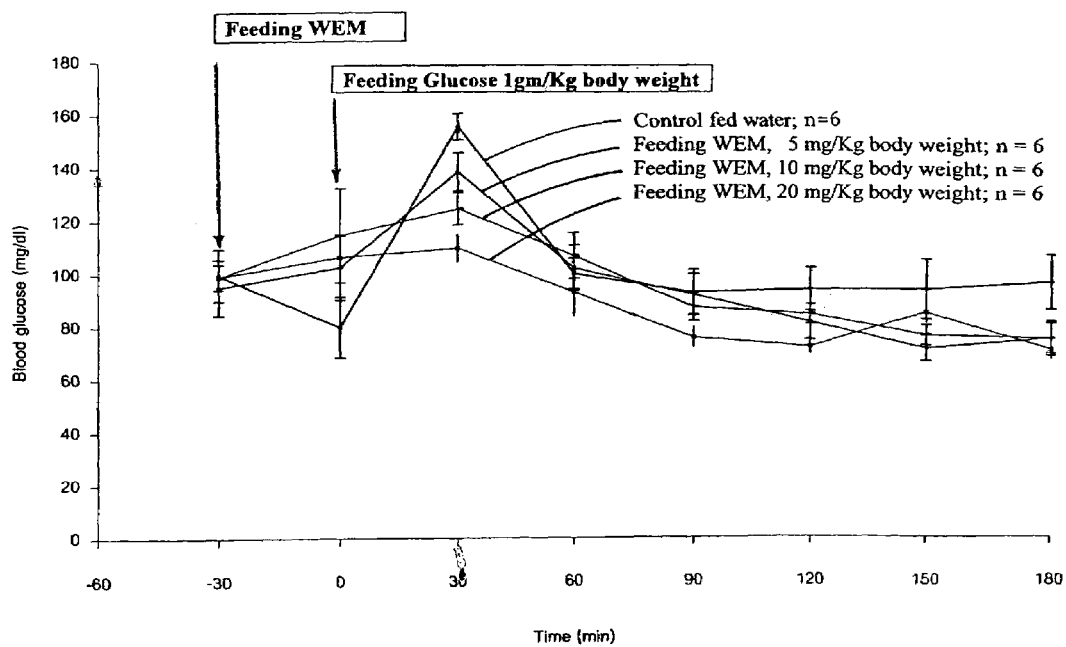
FIG. 1 illustrates hypoglycemic effect of water extract from dried leaves of *Malvastrum coromandelianum* (Linn.) Garcke, in normal Wistar rats, 100-125 grams body weight.

The two plant extracts used in this invention are prepared by extracting aerial parts, preferably, leaves, stems and branches of *Malvastrum coromandelianum* (Linn.) Garcke, Malvaceae and dried stems of *Coscinium fenestratum* (Gaerth.) Colebr., Menispermaceae; separately with water. The parts of plant used may be fresh or dried at 60 degree Celsius until constant dry weight is obtained. The dry ingredient is ground and put through a sieve to obtain powder of uniform particle size. Water is added to cover the powder using approximately 100 liters for 10 Kg dry weight of powder and the mixture is heated until boiled for five minutes and simmered at 80 degree Celsius for the next 7-8 hr. The filtrate is collected and the residual powder is further boiled in 50 liters water and simmered in similar manner once or twice. All filtrates are pooled and spray-dried, freeze-dried or concentrating-dried to obtain dried powder extract of the ingredient referred to as water extract of *M. coromandelianum* (Pinkish-light brown) or *C. fenestratum* (yellowish-brown). Generally, yield of 10% dry weight is obtained for each extract. Alternatively, aqueous organic solvent such as ethyl alcohol and water mixture may also be used instead of water although not quite as good. A similar extraction process is used to extract the plant ingredient to give the dried plant extract used in the present invention. The constituents in the dried plant extract are identified and quantitatively analyzed using conventional High Performance Liquid Chromatography (HPLC). The same method is used to quantify the amount of plant constituent to be mixed in the pharmaceutical preparations. Furthermore, in Thailand, the country of plant origin where these plants are grown and harvested, —the weather does not vary much during the year. Thus, there is not much difference between the crops harvested at different time of the year regarding the quality and the quantity of the constituents of the plant when analyzed by HPLC.

The dried plant extract is ground to fine powder and sieved to obtain uniform powder size and used for pharmaceutical preparation. The extract of plant *C. fenestratum* possesses good hypoglycemic and hypolipidemic activity in streptozotocin-induced diabetic rats while that of *M. coromandelianum* possesses very good hypoglycemic (FIG. 1) and good antimicrobial activity against several pathogenic microorganisms where Agar Diffusion Test was performed according to Lorian, V. Ed. (1991) Antibiotics in Laboratory Medicine, 3$^{rd}$ ed. The pathogenic microbes inhibited by the crude water extract of *M. coromandelianum* are *Staphylococcus aureus*, and *Salmonella typhimurium*. The glucose tolerance test showed very good hypoglycemic activity of the *M. coromandelianum* extract at 5 mg/kg body weight in normal rats as suppression of blood glucose level is distinct. Increasing amount of the extract to 10 and 20 mg/kg results in corresponding suppression of blood glucose level (FIG. 1).

These medicinal herb extracts can thus be used either singly or in combination in several ways. Firstly, it can be used as tea where dried ground coarse powder mixture of plant parts can be subjected to decoction by being boiled gently in water for a few minutes and the water extract is drunk on and off during the day. Alternatively, the coarse powder of dried ground leaves and stem can be packed in small bag made of heat-stable durable material with appropriate pore size to allow active ingredients of the plant to dissolve in hot water to be drunk as tea while retaining all the insoluble plant part within the bag. Secondly, the dried powder or granules of water extract can be served as hot instant beverage with or without flavoring or sweetening agent (not glucose nor sucrose nor energy-providing substances, i.e. non-sugar, non-carbohydrate, no-calories sweetener) which can be either aspartame or stevia, etc. By preparing as granule using appropriate pharmaceutical binder such as natural gums:-acacia, tragacanth, agar, starch mucilage, carrageenan or any appropriate synthetic binder, the extract can be used conveniently as instant tea. Thirdly, the granule or the extract powder can be formulated to be used as capsule or tablet to be given orally in various doses, 1-3 times daily depends on the health condition of a person. Other pharmaceutical dosage forms may also be applied such as non-sugar aqueous preparation or elixir to be given in equivalent doses. The water extract of the plant is the best way possible to use as extract from plant since the process is the simplest with no chance to be contaminated with organic solvent(s) which are much more expensive and can do harm to the environment including to human since even small amount of some organic solvents such as carbon tetrachloride or chloroform can cause ill effect(s) to a person especially to the liver, as well as can be very likely carcinogenic or may cause allergy.

In separating an extract solution from plant parts, the separation of an extract solution may be alternatively carried out according to a method such as pressing and centrifugal separation.

The extract solution obtained according to the above method may be alternatively condensed by means of a reverse osmosis membrane. This condensation by means of a reverse osmosis membrane has advantages that the active ingredients are preserved although most of them are quite heat-stable. The concentrate solution can be further dried by vacuum freeze-drying.

The preparation of the plant extract(s) having hypoglycemic, antimicrobial, with/without hypolipidemic activities can be any of the following examples.

EXAMPLE 1

Dried ground leaves (0.5-10.0 grams) of *M. coromandelianum* is immersed under 150-800 milliliters hot water (60-90° C.) for 5-10 minutes. Supernatant is decanted and can be drunk as herbal tea to maintain good health having blood sugar lowering activity. The water extract also has good antimicrobial activity against pathogenic microorganism, i.e. *S. aureus*.

EXAMPLE 2

Dried ground leaves (0.5-10.0 grams) of *M. coromandelianum* used singly or in combination with dried ground stems (0.5-20.0 grams) of *C. fenestratum* are immersed under 150-800 milliliters hot water (60-90° C.) for 5-10 minutes. Supernatant is decanted and can be drunk as herbal tea to maintain good health as blood sugar would be lowered to an appropriate level. The extracts in combination possess good hypoglycemic, hypolipidemic (both hypotriglyceridemic and hypocholesterolemic) and antimicrobial activities.

EXAMPLE 3

Dried ground leaves (0.5-10.0 grams) of *M. coromandelianum* is packed in porous, heat-stable bag and immersed under 150-800 milliliters hot water (60-90° C.) for 5-10 minutes. The bag is removed and the light yellow or brownish water extract can be drunk as tea.

EXAMPLE 4

Dried ground leaves (0.5-10.0 grams) of *M. coromandelianum* used singly or in combination with dried ground stems (0.5-20.0 grams) of *C. fenestratum* are packed in porous, heat-stable bag and immersed under 150-800 milliliters hot water (60-90° C.) for 5-10 minutes. The bag is removed and the yellow or brownish water extract can be drunk as tea all through the day.

EXAMPLE 5

Granulation of Plant Water Extracts

Water extract of *M. coromandelianum* or water extract of *C. fenestratum*, using 0.5-5% binders in the group of hydrocolloids and/or natural gum such as alginate, gum, agar, carrageenan, konjak flour, acacia, or tragacanth is granulated separately by conventional process for granulation, preferably, wet granulation.

Sieve the granules through sieve No. 30, collect the granules and dry at 50° Celsius until constant weight is obtained, kept under air-tight condition protected from light and moisture.

EXAMPLE 6

Herbal beverage with therapeutic properties-hypoglycemic, antimicrobial and hypolipidemic activities:

Granule of water extract of *M coromandelianum* is dissolved in water (0.01-10.0 grams, preferably 500 mg, of water extract per 150-800 ml) singly or in combination with granule of water extract of *C. fenestratum* (0.05-25.0 grams, preferably 1,000 mg, of water extract per 150-800 ml); to be drunk on and off during the day.

EXAMPLE 7

| | |
|---|---|
| Water extract of *M. coromandelianum* | 10-1,200 mg |
| Diluent | 75-175 mg |
| Lubricant | 10-20 mg |
| Binder | 2-5 mg |
| Total weight per capsule or tablet | 200-1,200 mg |

To be taken orally.

EXAMPLE 8

| | |
|---|---|
| Water extract of *M. coromandelianum* | 1,000 mg |
| Diluent | 175 mg |
| Lubricant | 20 mg |
| Binder | 5 mg |
| Total weight per capsule or tablet | 1,200 mg |

To be taken orally.

EXAMPLE 9

| | |
|---|---|
| Water extract of *M. coromandelianum* | 10-1,200 mg |
| Water extract of *Coscinium fenestratum* | 50-1,500 mg |
| Diluent | 75-175 mg |
| Lubricant | 10-20 mg |
| Binder | 2-15 mg |
| Total weight per capsule or tablet | 200-1,500 mg |

To be taken orally.

EXAMPLE 10

| | |
|---|---|
| Extract of *M. coromandelianum* | 600 mg |
| Extract of *C. fenestratum* | 750 mg |
| Diluent | 130 mg |
| Lubricant | 15 mg |
| Binder | 5 mg |
| Total weight per capsule or tablet | 1,500 mg |

To be taken orally.

For all the above examples:

The diluents used can be of any groups include: non-sweet, no or low calories, inert substance, preferably, microcrystalline cellulose, talcum, or corn starch, and where said diluents used may be only of one kind or mixture of several kinds in the range of 10 to 80% by weight;

The lubricants used can be of any groups include: mineral oil, fatty acid or its salt or vegetable oil, preferably, light mineral oil, hydrogenated vegetable oil, stearic acid, or stearate (Mg, Ca or Na), and where said lubricants used may be only of one kind or mixture of several kinds in the range of 1 to 15% by weight;

The binders used can be of any groups include: hydrocolloids and natural gum, preferably, alginate, gum, agar, carrageenan, konjak flour, acacia, tragacanth, and where said binders used may be only of one kind or mixture of several kinds in the range of 0.1 to 10% by weight; and The capsule used may be hard gelatin capsule or the like of appropriate size.

These pharmaceutical preparations are not limited to what has been described above, they can be any of other conventional preparations such as solution, reconstituted non-sugar liquid preparation and more of the appropriate dosage forms. They can be used to maintain good health in a normal person to keep blood sugar level not to exceed the desirable level. It can be also used in a diabetic person as it possesses all the desirable effects for diabetic patient, i.e. hypoglycemic effect, hypotriglyceridemic, hypocholesterolemic and good antimicrobial activity against various pathogenic microbes such as *S. aureus*, and *S. typhimurium*. It also appears to have good wound healing effect in man.

It will be understood that modifications may be made within the scope of this invention by one of ordinary skill in the art without departing from the spirit thereof. It is accordingly intended that all matter contained in the above description be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

We claim:

1. An orally administered botanical composition for maintaining good health in a normal person and a diabetic patient with hyperglycemia or hyperlipidemia whereby the composition also has antimicrobial activity against *Staphylococcus aureus*, wherein said botanical composition is formulated as capsule or tablet comprising:

| | |
|---|---|
| a water extract from dried leaves of *Malvastratum coromandelianum* | 10-1,200 mg |
| a water extract from dried stems of *Coscinium fenestratum* | 50-1,500 mg |
| Diluent | 75-175 mg |
| Lubricant | 10-20 mg |
| Binder | 2-5 mg |
| Total weight per capsule or tablet | 200-1,500 mg. |

2. The botanical composition according to claim 1 comprising:

| | |
|---|---|
| a water extract from dried leaves of *Malvastratum coromandelianum* | 600 mg |
| a water extract from dried stems of *Coscinium fenestratum* | 750 mg |
| Diluent | 130 mg |
| Lubricant | 15 mg |
| Binder | 5 mg |
| Total weight per capsule or tablet | 1,500 mg. |

3. An orally administered botanical composition for maintaining good health in a normal person and a diabetic patient with hyperglycemia whereby the composition also has antimicrobial activity against *Staphylococcus aureus*, wherein said botanical composition is formulated as capsule or tablet comprising:

| | |
|---|---|
| a water extract from dried leaves of *Malvastratum coromandelianum* | 10-1,200 mg |
| Diluent | 75-175 mg |
| Lubricant | 10-20 mg |
| Binder | 2-5 mg |
| Total weight per capsule or tablet | 200-1,200 mg. |

4. The botanical composition according to claim 3 comprising:

| | |
|---|---|
| a water extract from dried leaves of *Malvastratum coromandelianum* | 1,000 mg |
| Diluent | 175 mg |
| Lubricant | 20 mg |
| Binder | 5 mg |
| Total weight per capsule or tablet | 1,200 mg. |

* * * * *